US012758087B2

(12) United States Patent
Wales et al.

(10) Patent No.: US 12,758,087 B2
(45) Date of Patent: Oct. 13, 2026

(54) WATER RESERVOIR INCLUDING A FLEXIBLE EXTENSION

(71) Applicant: Boston Scientific Scimed, Inc., Maple Grove, MN (US)

(72) Inventors: Ryan V. Wales, Northborough, MA (US); Colby Harris, Norfolk, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 390 days.

(21) Appl. No.: 18/454,545

(22) Filed: Aug. 23, 2023

(65) Prior Publication Data

US 2024/0065537 A1 Feb. 29, 2024

Related U.S. Application Data

(60) Provisional application No. 63/401,443, filed on Aug. 26, 2022.

(51) Int. Cl.

| | |
|---|---|
| ***A61B 1/00*** | (2006.01) |
| ***A61B 1/015*** | (2006.01) |
| ***A61B 1/12*** | (2006.01) |
| ***B05B 7/24*** | (2006.01) |
| ***B05B 9/04*** | (2006.01) |

(Continued)

(52) U.S. Cl.

CPC .......... *A61B 1/015* (2013.01); *A61B 1/00128* (2013.01); *A61B 1/00131* (2013.01); *A61B 1/126* (2013.01); *B05B 7/2418* (2013.01); *B05B 7/2427* (2013.01); *B05B 9/0403* (2013.01); *B05B 12/002* (2013.01); *B05B 15/63* (2018.02)

(58) Field of Classification Search

None

See application file for complete search history.

(56) References Cited

U.S. PATENT DOCUMENTS

| | | | |
|---|---|---|---|
| 4,236,655 | A | 12/1980 | Humpries |
| 5,174,343 | A | 12/1992 | Rood |

(Continued)

FOREIGN PATENT DOCUMENTS

| | | | |
|---|---|---|---|
| EP | 0157673 | A1 | 10/1985 |
| GB | 2483850 | A | 3/2012 |

(Continued)

OTHER PUBLICATIONS

International Search Report and Written Opinion dated Dec. 21, 2023 for International Application No. PCT/US2023/072727.

*Primary Examiner* — Levon J Shahinian

(74) *Attorney, Agent, or Firm* — Seager, Tufte & Wickhem, LLP

(57) ABSTRACT

Methods and systems for supplying gas and water to an endoscope system. An illustrative container and tube set may comprise a container configured to contain a fluid and having a bottom portion and a top portion, a lens water supply tube including a first end, a second end, and a first lumen extending therethrough, a gas supply tube including a first end, a second end, and a second lumen extending therethrough, a port positioned adjacent to the top portion of the container, and a flexible tube including a first end coupled to the top portion of the container, a second end, and a third lumen extending therethrough. The third lumen of the flexible tube may be configured to be in selective fluid communication with the interior of the container.

14 Claims, 9 Drawing Sheets

(51) Int. Cl.

| | |
|---|---|
| ***B05B 12/00*** | (2018.01) |
| ***B05B 15/63*** | (2018.01) |

(56) References Cited

U.S. PATENT DOCUMENTS

| | | | | |
|---|---|---|---|---|
| 2006/0106285 | A1 | 5/2006 | Boulais et al. | |
| 2007/0043262 | A1 | 2/2007 | Levy et al. | |
| 2018/0265345 | A1 * | 9/2018 | Marshall .............. | A47K 5/1202 |
| 2019/0255546 | A1 | 8/2019 | Sokolowski | |
| 2022/0192478 | A1 | 6/2022 | Pollock et al. | |

FOREIGN PATENT DOCUMENTS

| | | | |
|---|---|---|---|
| JP | 2021-523852 | A | 9/2021 |
| WO | 2009146515 | A1 | 12/2009 |
| WO | 2018170059 | A1 | 9/2018 |
| WO | 2019226094 | A1 | 11/2019 |

* cited by examiner

WATER RESERVOIR INCLUDING A FLEXIBLE EXTENSION

CROSS-REFERENCE TO RELATED APPLICATIONS

This application claims the benefit of U.S. Provisional Patent Application Ser. No. 63/401,443 filed on Aug. 26, 2022, the disclosure of which is incorporated herein by reference.

FIELD

This disclosure relates generally to medical fluid containers and methods, and particularly to a container and tube sets to supply fluid and/or gas to an endoscope.

BACKGROUND

Conventionally, endoscope devices have been widely used for performing diagnostic and/or therapeutic treatments. During endoscopic procedures, physicians may use a combination of air, irrigation and lens wash as a means of flushing debris, cleaning optics, and insufflating the working lumen. To enable these capabilities compressed gasses from either the processor or alternative source are used to insufflate the working lumen or increase the pressure within a fluid bottle which washes the lens of the endoscope. Additionally, a peristaltic pump can be used to irrigate the working lumen of debris. One of the challenges faced during endoscopic procedures is that the common water bottle and tube set used contain a maximum of 1 liter of water and are not designed to be refilled. This may force nurses/technicians to replace the water bottle multiple times a day. This may introduce multiple opportunities for contamination to the tube set by either contacting non-sterile surfaces or dropping the tubing on the floor. It is with these considerations in mind that the improvements of the present disclosure may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

In a first example, a container arranged and configured to couple to an endoscope for use in an endoscopic procedure may comprise a container configured to contain a fluid and having a bottom portion and a top portion, a lens water supply tube including a first end, a second end, and a first lumen extending therethrough, wherein the first lumen is in fluid communication with the bottom portion of the container and the second end of the lens water supply tube is positioned external to the container, a gas supply tube including a first end, a second end, and a second lumen extending therethrough, wherein the second lumen is in operative fluid communication with an interior of the container and the second end of the gas supply tube is positioned external to the container, a port positioned adjacent to the top portion of the container, and a flexible tube including a first end coupled to the top portion of the container, a second end, and a third lumen extending therethrough, wherein the third lumen of the flexible tube is configured to be in selective fluid communication with the interior of the container.

Alternatively or additionally to the example above, in another example, the second end of the flexible tube may be configured to be selectively coupled to the port.

Alternatively or additionally to any of the examples above, in another example, the second end of the flexible tube may be configured to threadably engage the port.

Alternatively or additionally to any of the examples above, in another example, the second end of the flexible tube may include a rotatable collar.

Alternatively or additionally to any of the examples above, in another example, the port may include a plurality of external threads.

Alternatively or additionally to any of the examples above, in another example, the first end of the flexible tube may be rotatably coupled to the container.

Alternatively or additionally to any of the examples above, in another example, the second end of the flexible tube may comprise an annular sealing plug in fluid communication with the third lumen of the flexible tube.

Alternatively or additionally to any of the examples above, in another example, the annular sealing plug may be configured to form a seal with a water bottle.

Alternatively or additionally to any of the examples above, in another example, the annular sealing plug may be configured to be disposed within a mouth of the water bottle and may be configured to form the seal with the mouth of the water bottle.

Alternatively or additionally to any of the examples above, in another example, an external surface of the annular sealing plug may have a taper.

Alternatively or additionally to any of the examples above, in another example, the taper may be a conic taper.

Alternatively or additionally to any of the examples above, in another example, the annular sealing plug may be configured to be disposed over a mouth of the water bottle and may be configured to form the seal with the mouth of the water bottle.

Alternatively or additionally to any of the examples above, in another example, an interior surface of the annular sealing plug may have a taper.

Alternatively or additionally to any of the examples above, in another example, the taper may be a conic taper.

Alternatively or additionally to any of the examples above, in another example, the container may further comprise an actuatable cap disposed over the annular sealing plug.

Alternatively or additionally to any of the examples above, in another example, the actuatable cap may be configured to be opened to transfer water from a water bottle to the container and closed during use of the container.

Alternatively or additionally to any of the examples above, in another example, when the second end of the flexible tube is coupled to the port, the flexible tube may form a handle.

Alternatively or additionally to any of the examples above, in another example, when the second end of the flexible tube is free from the port, the second end of the flexible tube may be configured to be coupled to a water bottle.

Alternatively or additionally to any of the examples above, in another example, the port may be recessed into the top portion of the container.

In another example, a container arranged and configured to couple to an endoscope for use in an endoscopic procedure may comprise a container configured to contain a fluid and having a bottom portion and a top portion, a lens water supply tube including a first end, a second end, and a first lumen extending therethrough, wherein the first lumen is in fluid communication with the bottom portion of the container and the second end of the lens water supply tube is positioned external to the container, a gas supply tube including a first end, a second end, and a second lumen extending therethrough, wherein the second lumen is in operative fluid communication with an interior of the container and the second end of the gas supply tube is positioned external to the container, a port positioned adjacent to the top portion of the container, and a flexible tube including a first end coupled to the top portion of the container, a second end, and a third lumen extending therethrough, wherein the third lumen of the flexible tube is configured to be in selective fluid communication with the interior of the container. The second end of the flexible tube may be configured to be selectively coupled to the port and when the second end of the flexible tube is coupled to the port, the flexible tube may form a handle.

Alternatively or additionally to any of the examples above, in another example, the second end of the flexible tube may be configured to threadably engage the port.

Alternatively or additionally to any of the examples above, in another example, the second end of the flexible tube may include a rotatable collar.

Alternatively or additionally to any of the examples above, in another example, the port may include a plurality of external threads.

Alternatively or additionally to any of the examples above, in another example, the first end of the flexible tube may be rotatably coupled to the container.

Alternatively or additionally to any of the examples above, in another example, when the second end of the flexible tube is free from the port, the second end of the flexible tube may be configured to be coupled to a water bottle.

In another example, a container arranged and configured to couple to an endoscope for use in an endoscopic procedure may comprise a container configured to contain a fluid and having a bottom portion and a top portion, a lens water supply tube including a first end, a second end, and a first lumen extending therethrough, wherein the first lumen is in fluid communication with the bottom portion of the container and the second end of the lens water supply tube is positioned external to the container, a gas supply tube including a first end, a second end, and a second lumen extending therethrough, wherein the second lumen is in operative fluid communication with an interior of the container and the second end of the gas supply tube is positioned external to the container, a port positioned adjacent to the top portion of the container, and a flexible tube including a first end coupled to the top portion of the container, a second end comprising an annular sealing plug, a third lumen extending therethrough, wherein the third lumen of the flexible tube is configured to be in selective fluid communication with the interior of the container. The annular sealing plug may comprise a deformable material.

Alternatively or additionally to any of the examples above, in another example, the annular sealing plug may be configured to form a seal with a water bottle.

Alternatively or additionally to any of the examples above, in another example, the container may further comprise an actuatable cap disposed over the annular sealing plug.

Alternatively or additionally to any of the examples above, in another example, the actuatable cap may be configured to be opened to transfer water from a water bottle to the container and closed during use of the container.

Alternatively or additionally to any of the examples above, in another example, the actuatable cap may comprise a hinged cap.

Alternatively or additionally to any of the examples above, in another example, the actuatable cap may comprise a sliding cap.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various exemplary embodiments and together with the description serve to explain the principles of the present disclosure.

Figure 1:
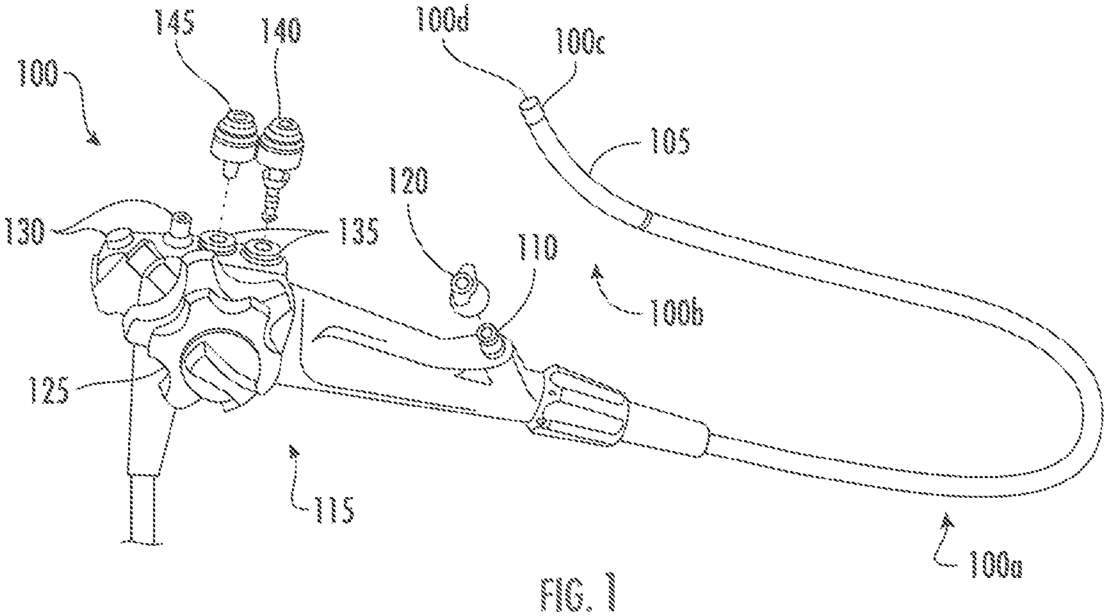
FIG. 1 depicts components of an endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure is now described with reference to an exemplary medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, the same or similar reference numbers will be used through the drawings to refer to the same or like parts.

The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately" and "substantially" indicate a range of values within +/−10% of a stated or implied value. Additionally, terms that indicate the geometric shape of a component/surface refer to exact and approximate shapes.

Embodiments of the present disclosure are described with specific reference to a bottle (e.g., container, reservoir, or the like) and tube assembly or set. It should be appreciated that such embodiments may be used to supply fluid and/or gas to an endoscope, for a variety of different purposes, including, for example to facilitate insufflation of a patient, lens washing, and/or to irrigate a working channel to aid in flushing/suctioning debris during an endoscopic procedure.

Although the present disclosure includes descriptions of a container and tube set suitable for use with an endoscope system to supply fluid and/or gas to an endoscope, the devices, systems, and methods herein could be implemented in other medical systems requiring fluid and/or gas delivery, and for various other purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Conventionally, endoscope devices have been widely used for performing diagnostic and/or therapeutic treatments. During endoscopic procedures, physicians may use a combination of air, irrigation and lens wash as a means of flushing debris, cleaning optics, and insufflating the working lumen. To enable these features, the endoscope umbilicus is connected to a water bottle via a set of tubes. One of the tubes sends pressurized air from the processor to the water bottle. Another tube is a water tube that is suspended at the bottom of the bottle within the water. To ensure that the tube stays at the bottom of the water bottle, a weight may be coupled to the distal tip to keep the tube from floating to the top of the water surface. Additionally, at the top of the bottle, a cap is fitted with multiple features and parts to ensure that the preferred performance is achieved. Disclosed herein are containers and tube sets which combing multiple parts and features into one part which may reduce the number of parts needed to achieve the same performance.

Figure 2:
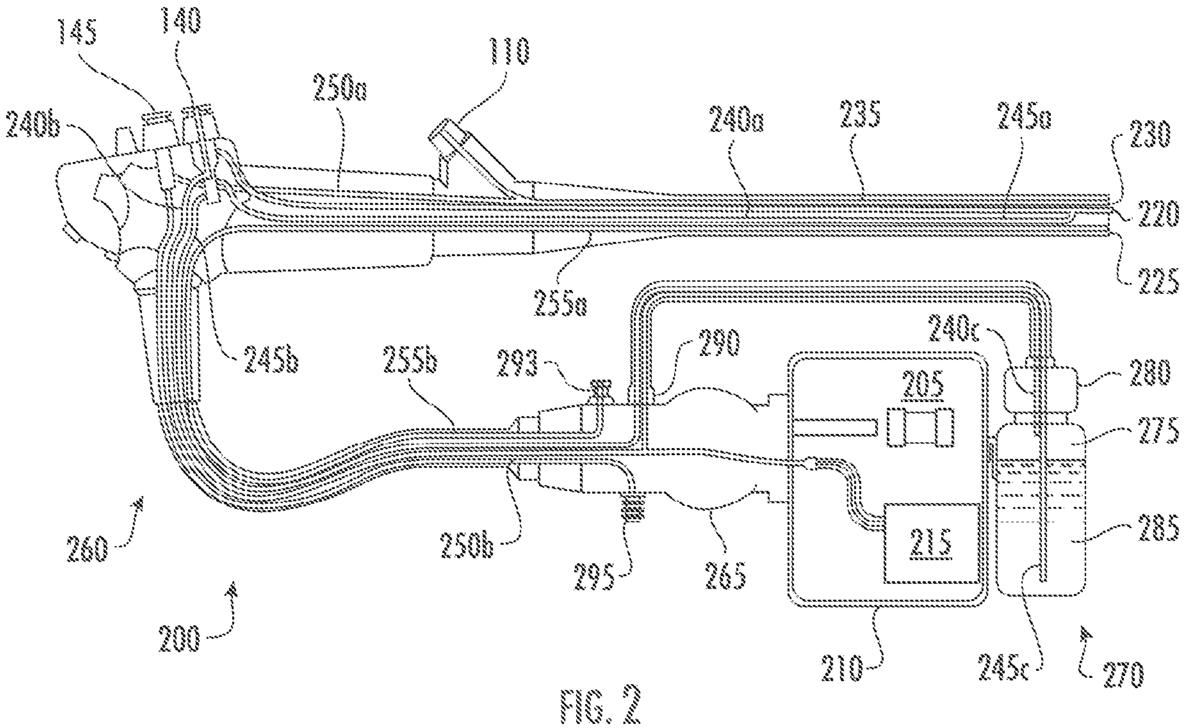
FIG. 2 depicts components of an endoscope system with endoscope, light source, light source connector, water reservoir, and tubing assembly for air and lens wash fluid delivery.

With reference to FIGS. 1-2, an exemplary endoscope 100 and system 200 are depicted that may comprise an elongated shaft 100*a* that is inserted into a patient. A light source 205 feeds illumination light to a distal portion 100*b* of the endoscope 100, which may house an imager (e.g., CCD or CMOS imager) (not shown). The light source 205 (e.g., lamp) is housed in a video processing unit 210 that processes signals that are input from the imager and outputs processed video signals to a video monitor (not shown) for viewing. The video processing unit 210 also serves as a component of an air/water feed circuit by housing a pressurizing pump 215, such as an air feed pump, in the unit.

The endoscope shaft 100*a* may include a distal tip 100*c* provided at the distal portion 100*b* of the shaft 100*a* and a flexible bending portion 105 proximal to the distal tip 100*c*. The flexible bending portion 105 may include an articulation joint (not shown) to assist with steering the distal tip 100*c*. On an end face 100*d* of the distal tip 100*c* of the endoscope 100 is a gas/lens wash nozzle 220 for supplying gas to insufflate the interior of the patient at the treatment area and for supplying water to wash a lens covering the imager. An irrigation opening 225 in the end face 100*d* supplies irrigation fluid to the treatment area of the patient. Illumination windows (not shown) that convey illumination light to the treatment area, and an opening 230 to a working channel 235 extending along the shaft 100*a* for passing tools to the treatment area, may also be included on the face 100*d* of the distal tip 100*c*. The working channel 235 extends along the shaft 100*a* to a proximal channel opening 110 positioned distal to an operating handle 115 of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle 115 is provided with dual valve wells 135. One of the valve wells 135 may receive a gas/water valve 140 for operating an insufflating gas and lens water feed operation. A gas supply line 240*a* and a lens wash supply line 245*a* run distally from the gas/water valve 140 along the shaft 100*a* and converge at the distal tip 100*c* proximal to the gas/wash nozzle 220 (FIG. 2). The other valve well 135 receives a suction valve 145 for operating a suction operation. A suction supply line 250*a* runs distally from the suction valve 145 along the shaft 100*a* to a junction point in fluid communication with the working channel 235 of the endoscope 100.

The operating handle 115 is electrically and fluidly connected to the video processing unit 210, via a flexible umbilical 260 and connector portion 265 extending therebetween. The flexible umbilical 260 has a gas (e.g., air or $CO_2$) feed line 240*b*, a lens wash feed line 245*b*, a suction feed line 250*b*, an irrigation feed line 255*b*, a light guide (not shown), and an electrical signal cable (not shown). The connector portion 265 when plugged into the video processing unit 210 connects the light source 205 in the video processing unit with the light guide. The light guide runs along the umbilical 260 and the length of the endoscope shaft 100*a* to transmit light to the distal tip 100*c* of the endoscope 100. The connector portion 265 when plugged into the video processing unit 210 also connects the air pump 215 to the gas feed line 240*b* in the umbilical 260.

A water reservoir or container 270 (e.g., water bottle) is fluidly connected to the endoscope 100 through the connector portion 265 and the umbilical 260. A length of gas supply tubing 240*c* passes from one end positioned in an air gap 275 between the top 280 (e.g., bottle cap) of the reservoir 270 and the remaining water 285 in the reservoir to a detachable gas/lens wash connection 290 on the outside of the connector portion 265. The detachable gas/lens wash connection 290 may be detachable from the connector portion 265 and/or the gas supply tubing 240*c*. The gas feed line 240*b* from the umbilical 260 branches in the connector portion 265 to fluidly communicate with the gas supply tubing 240*c* at the detachable gas/lens wash connection 290, as well as the air pump 215. A length of lens wash tubing 245*c*, with one end positioned at the bottom of the reservoir 270, passes through the top 280 of the reservoir 270 to the same detachable connection 290 as the gas supply tubing 240*c* on the connector portion 265. In other embodiments, the connections may be separate and/or separated from each other. The connector portion 265 also has a detachable irrigation connection 293 for irrigation supply tubing (not shown) running from a source of irrigation water (not shown) to the irrigation feed line 255*b* in the umbilical 260. The detachable irrigation connection 293 may be detachable from the connector portion 265 and/or the irrigation supply tubing (not shown). In some embodiments, irrigation water is supplied via a pump (e.g., peristaltic pump) from a water source independent (not shown) from the water reservoir 270. In other embodiments, the irrigation supply tubing and lens wash tubing 245*c* may source water from the same reservoir. The connector portion 265 may also include a detachable suction connection 295 for suction feed line 250*b* and suction supply line 250*a* fluidly connecting a vacuum source (e.g., hospital house suction) (not shown) to the umbilical 260 and endoscope 100. The detachable suction connection 295 may be detachable from the connector portion 265 and/or the suction feed line 250*b* and/or the vacuum source.

The gas feed line 240*b* and lens wash feed line 245*b* are fluidly connected to the valve well 135 for the gas/water valve 140 and configured such that operation of the gas/water valve in the well controls supply of gas or lens wash to the distal tip 100*c* of the endoscope 100. The suction feed line 250*b* is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the video processing unit 210 is flowed through the connector portion 265 and branched to the gas/water valve 140 on the operating handle 115 through the gas feed line 240*b* in the umbilical 260, as well as through the gas supply tubing 240*c* to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240*a* and out the distal tip 100*c* of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash tubing 245*c*, through the connector portion 265, umbilical 260, through the gas/water valve 140 and down the lens wash supply line 245*a*, converging with the gas supply line 240*a* prior to exiting the distal tip 100*c* of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash tubing 245*c*, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240*c* to filter-out undesired contaminants or particulates from passing into the water reservoir 270. In some embodiments, outflow check valves or other one-way valve configurations (not shown) may be placed in the path of the lens wash supply tubing to help prevent water from back-flowing into the reservoir 270 after the water has passed the valve.

A relatively higher flow rate of irrigation water is typically required compared to lens wash, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the top of the water source and threaded through the head on the upstream side of the pump. Tubing on the downstream side of the pump is connected to the irrigation feed line 255*b* in the umbilical 260 and the irrigation supply line 255*a* endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255*b* in the umbilical, and down the irrigation supply line in the shaft 100*a* of the endoscope to the distal tip 100*c*. In order to equalize the pressure in the water source as water is pumped out of the irrigation supply tubing, an air vent (not shown)

may be included in the top 280 of the water reservoir 270. The vent allows atmospheric air into the water source preventing negative pressure build-up in the water source, which could create a vacuum that suctions undesired matter from the patient back through the endoscope toward the water source. In some embodiments, outflow check valves or other one-way valve configurations (not shown), similar to the lens wash tubing 245*c*, may be placed in the path of the irrigation supply tubing to help prevent back-flow into the reservoir after water has passed the valve.

FIGS. 3A-3D are schematic drawings illustrating the operation of an embodiment of a hybrid system 300 where the supply tubing for irrigation and lens wash are connected to and drawn from a single water reservoir. It is contemplated that fluids other than water may be used, such as, but not limited to saline. The hybrid system 300 includes the single water reservoir 305, a cap 310 for the reservoir, gas supply tubing 240*c*, lens wash supply tubing 245*c*, irrigation pump 315 with foot switch 318, upstream supply tubing for irrigation 320 and downstream irrigation supply tubing 255*c*. The cap 310 may be configured to attach in a seal-tight manner to the water reservoir 305 by a typically threaded arrangement. The cap 310 may include a gasket to seal the cap 310 to the reservoir 305. The gasket can be an O-ring, flange, collar, and/or the like and can be formed of any suitable material. A number of through-openings (325*a*, 325*b*, 325*c*) in the cap 310 are provided to receive, respectively, the gas supply tubing 240*c*, lens wash supply tubing 245*c*, and upstream irrigation supply tubing 320. In FIGS. 3A-3D, the system depicted includes separate tubing for gas supply, lens wash, and irrigation.

In other embodiments, the gas supply tubing 240*c* and lens wash tubing 245*c* may be combined in a coaxial arrangement. Some illustrative coaxial arrangements are described in commonly assigned U.S. patent application Ser. No. 17/558,239, titled INTEGRATED CONTAINER AND TUBE SET FOR FLUID DELIVERY WITH AN ENDOSCOPE and U.S. patent application Ser. No. 17/558,256, titled TUBING ASSEMBLIES AND METHODS FOR FLUID DELIVERY, the disclosures of which are hereby incorporated by reference. For example, the gas supply tubing may define a lumen that is sufficiently large in diameter to encompass a smaller diameter lens wash tubing, coaxially received within the gas supply tubing, as well as provide air to the water source in an annular space surrounding the lens wash tubing to pressurize the water reservoir (see, e.g., gas and lens wash supply tubing 240*c*, 245*c*). The lens wash supply tubing may be configured to exit the lumen defined by the coaxial gas supply tubing in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion (e.g., connector portion 265 of FIG. 2).

In various embodiments, different configurations of valving (not shown) may be incorporated into various embodiments disclosed hereby, including the tubing of the system 200, 300. For example, an in-flow check valve can be disposed in the path of the gas supply tubing 240*c* to help prevent backflow into the air pump 215. In this manner, pressure building within the water reservoir 305 creates a pressure difference between the water source and the gas supply tubing 240*c* helping to maintain a positive pressure in the water source even when large amounts of water may be removed from the water source during the irrigation function. This arrangement compensates for any time lag in air being delivered from the air pump 215 to the water reservoir 305, which might otherwise cause a negative pressure vacuum in the water reservoir. Similarly, an outflow check valve, such as the one-way valve with inlet/outlets and valve insert, may be incorporated in the lens wash supply tubing 245*c*, upstream irrigation supply tubing 320, and/or downstream irrigation supply tubing 255*c* to help prevent backflow of water from either or both of the lens wash and supply tubing for irrigation in the event of a negative pressure situation, as described.

More generally, in many embodiments, a check valve may refer to any type of configuration for fluid to flow only in one direction in a passive manner. For example, a check valve may include, or refer to, one or more of a ball check valve, a diaphragm check valve, a swing check valve, a tilting disc check valve, a flapper valve, a stop-check valve, a lift-check valve, an in-line check valve, a duckbill valve, a pneumatic non-return valve, a reed valve, a flow check. Accordingly, a check valve as used herein is meant to be separate and distinct from an active valve that is operated in a binary manner as an on/off valve or switch to allowed flow to be turned on or allow flow to be turned off (e.g., a stop cock valve, solenoid valve, peristaltic pump).

During operation of the system of FIGS. 3A-3D, a flow of water for irrigation may be achieved by operating the irrigation pump 315. A flow of water for lens wash may be achieved by depressing the gas/water valve 140 on the operating handle 115 of the endoscope 100. These functions may be performed independent of one another or simultaneously. When operating lens wash and irrigation at the same time, as fluid is removed from the water reservoir 305, the pressure in the system may be controlled to maintain the lens wash supply tubing 245*c* at substantially the pressure necessary to accomplish a lower flow rate lens wash, while compensating for reduced pressure in the water reservoir 305 due to supplying a high flow rate irrigation. When pressure is reduced in the water reservoir by use of the lens wash function, the irrigation function, or both functions simultaneously, the reduced pressure may be compensated for by the air pump 215 via the gas supply tubing 240*c*.

Figure 3A:
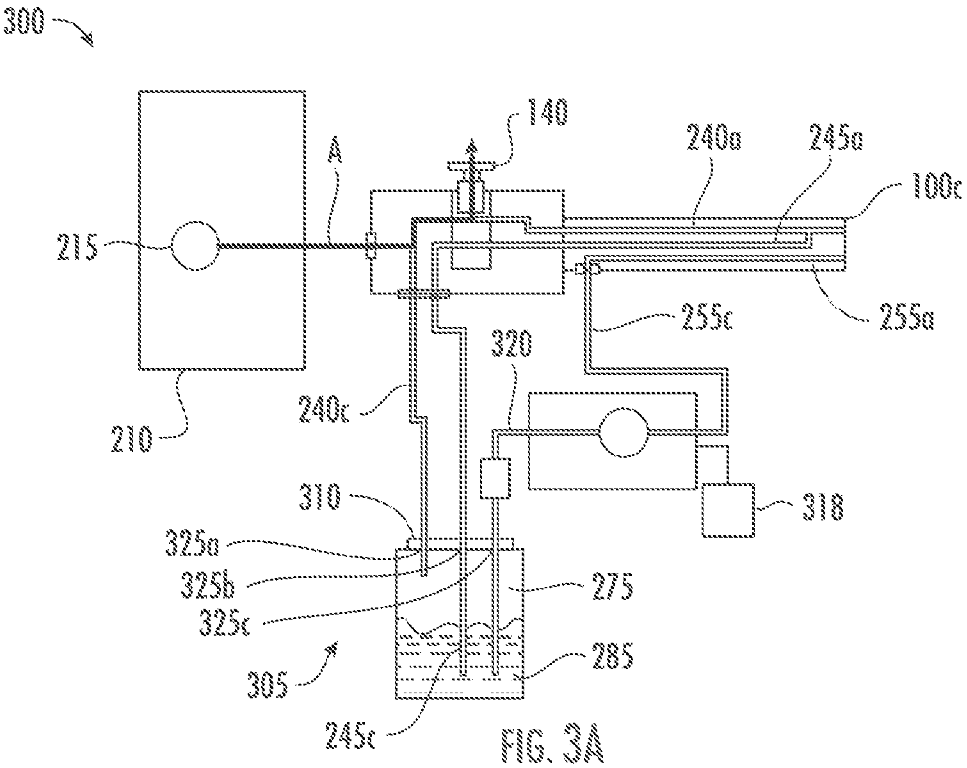
FIG. 3A depicts an endoscope system with endoscope, light source, water reservoir, and tubing assembly for hybrid air, lens wash and irrigation fluid delivery, wherein the system is activated to deliver air to atmosphere.

The schematic set-up in FIGS. 3A-3D has been highlighted to show the different flow paths possible with the hybrid system 300 having supply tubing for irrigation 320 and lens wash supply tubing 245*c* connected to and drawn from the single water reservoir 305. As shown in FIG. 3A, the endoscope 100 is in a neutral state with the gas/water valve 140 in an open position. The neutral state delivers neither gas, nor lens wash, to the distal tip of the endoscope. Rather gas (pressure) is delivered along path A from the pressurizing air pump 215 and vented through the gas feed line 240*b* in the umbilical 260 via the connector portion 265 and through the gas/water valve to atmosphere. Since the system is open at the vent hole in the gas/water valve 140, there is no build up to pressurize the water reservoir 305 and consequently no water is pushed through the lens wash supply tubing 245*c*.

Figure 3B:
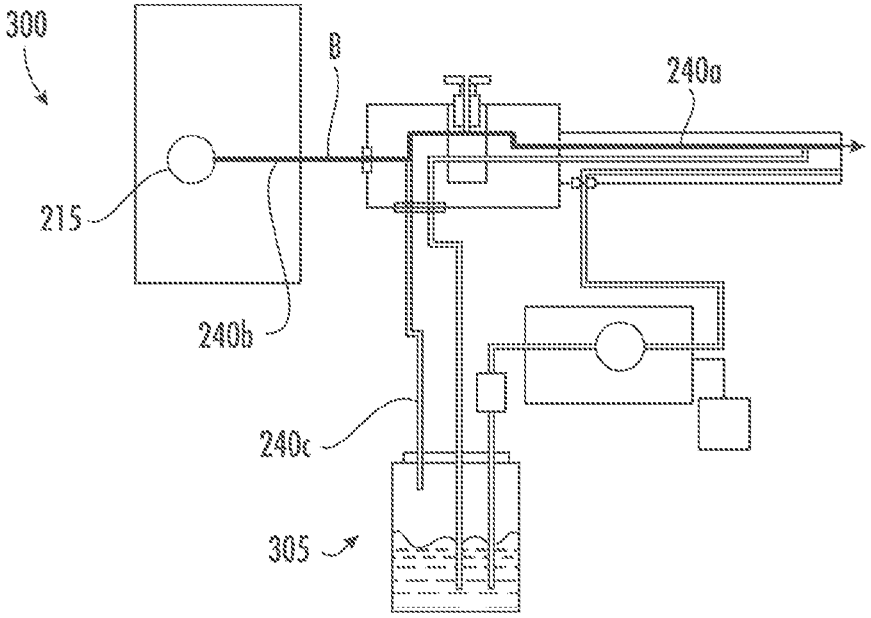
FIG. 3B depicts the endoscope system of FIG. 3A, wherein the system is activated to deliver air to a patient through the patient end of the endoscope.

As shown in FIG. 3B, the endoscope 100 is in a gas delivery state with the gas/water valve 140 in a first position. When gas is called for at the distal tip 100*c*, for example, to clean the end face 100*d* of the distal tip or insufflate the patient body in the treatment area, the user closes off the vent hole in the gas/water valve 140 with a thumb, finger, or the like (first position). In this state, gas (pressure) is delivered along path B from the air pump 215 and flowed through the gas feed line 240*b* in the umbilical 260 via the connector portion 265. The gas continues through the gas/water valve 140 to the gas supply line 240*a* in the endoscope shaft 100*a* and out the gas/lens wash nozzle 220 at the distal tip 100*c*.

There is no build up to pressurize the water reservoir since the system is open at the gas/lens water nozzle 220, and consequently no water is pushed through the lens wash supply tubing 245*c*.

Figure 3C:
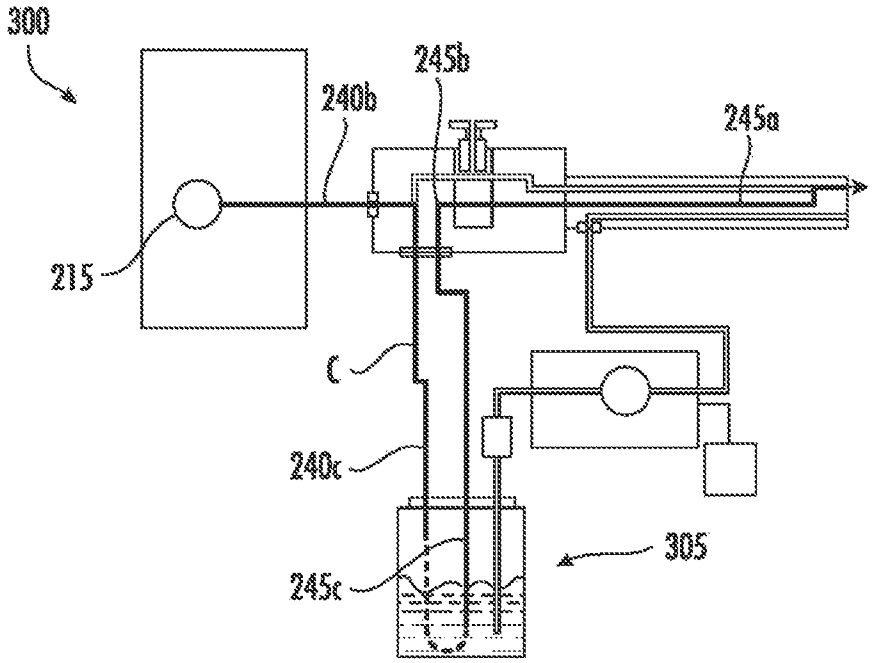
FIG. 3C depicts the endoscope system of FIG. 3A, wherein the system is activated to deliver lens wash fluid through the patient end of the endoscope.

As shown in FIG. 3C, the endoscope 100 is in a lens wash delivery state with the gas/water valve 140 in a second position. When lens wash is called for at the distal tip 100*c*, for example, to clean the end face 100*d* of the distal tip 100*c*, the user, keeping the vent hole in the air/water valve closed off, depresses the valve 140 to its furthest point in the valve well 135. The second position blocks off the gas supply to both atmosphere and the gas supply line 240*a* in the endoscope, and opens up the gas/water valve 140 to allow lens wash water to pass through to the lens wash supply line 245*a* in the endoscope shaft 100*a* and out the gas/lens wash nozzle 220 at the distal tip 100*c*. In this state, gas (pressure) is delivered along path C from the air pump 215, through the branched line in the connector portion 265 and out of the gas supply tubing 240*c* to the water reservoir 305. The gas (pressure) pressurizes the surface of the remaining water 285 in the reservoir 305 and pushes water up the lens wash supply tube 245*c* to the connector portion 265. The pressurized lens wash water is pushed further through the lens wash feed line 245*b* in the umbilical 260 and through the gas/water valve 140. Since the system 300 is closed, gas pressure is allowed to build and maintain a calibrated pressure level in the water reservoir 305, rather than venting to atmosphere or being delivered to the patient. This pressure, along with the endoscope feed and supply lines and external tubing, translates to a certain range of flow rate of the lens wash.

Figure 3D:
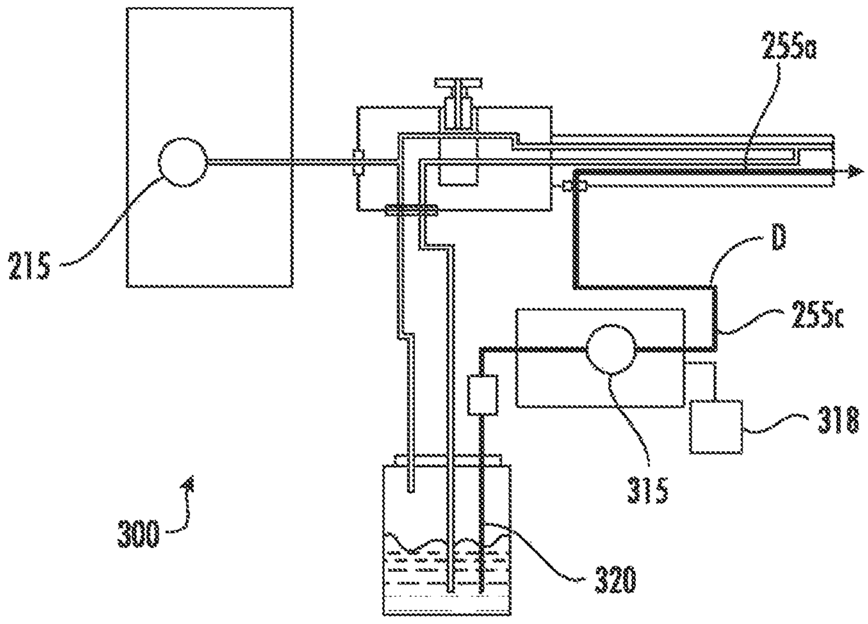
FIG. 3D depicts the endoscope system of FIG. 3A, wherein the system is activated to deliver irrigation fluid through the patient end of the endoscope.

As shown in FIG. 3D, the endoscope 100 is in an irrigation delivery state. This may be performed at the same or a different time from the delivery of gas and/or lens wash. When irrigation is called for at the distal tip 100*c*, for example, if visibility in the treatment area is poor or blocked by debris, or the like, the user activates the irrigation pump 315 (e.g., by depressing foot switch 318) to delivery water along path D. With the pump 315 activated, water is sucked out of the water reservoir 305 through the upstream irrigation supply tubing 320 and pumped along the downstream irrigation supply tubing 255*c* to the connector portion 265. The irrigation pump head pressure pushes the irrigation water further through the irrigation feed line 255*b* in the umbilical 260, through the irrigation supply line 255*a* in the endoscope shaft 100*a*, and out the irrigation opening 225 at the distal tip 100*c*. The irrigation pump pressure may be calibrated, along with the endoscope irrigation feed and supply lines and external tubing, to deliver a certain range of flow rate of the irrigation fluid.

Figure 4:
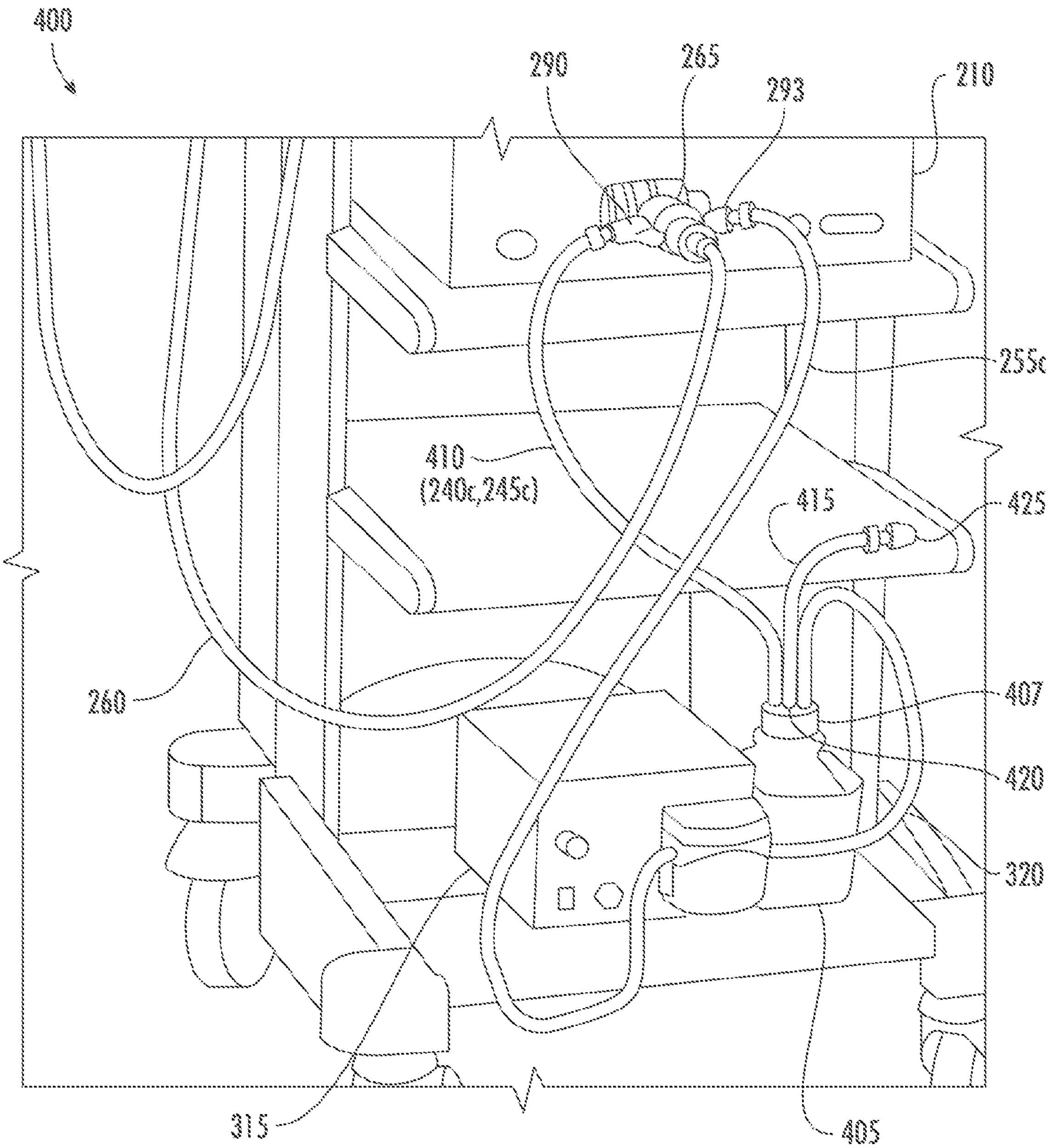
FIG. 4 depicts a hybrid endoscope system including a video processing unit, connector portion, peristaltic irrigation pump, water reservoir and top, coaxial gas and lens wash supply tubing, upstream and downstream irrigation supply tubing, and alternative gas supply tubing.

FIG. 4 is a schematic drawing illustrating a further embodiment of a hybrid system 400 including a video processing unit 210, connector portion 265, peristaltic irrigation pump 315, water reservoir 405 and top 407, coaxial gas and lens wash supply tubing 410, upstream and downstream irrigation supply tubing 320, 255*c*, respectively, and alternative gas (e.g., $CO_2$) supply tubing 415. A length of the alternative gas supply tubing 415 passes from one end positioned in the gas gap 275 (see FIG. 2) between the top 407 of the water reservoir 405 and the remaining water 285 in the reservoir through an additional opening 420 in the top of the reservoir to a detachable connection 425 for a source of the alternative gas supply (e.g., $CO_2$ hospital house gas source). When the alternative gas supply is desired, such as $CO_2$ gas, the air pump 215 on the video processing unit 210 may be turned off and $CO_2$ gas, rather than air, is thereby flowed to the water reservoir 405 pressurizing the water surface. Generally, the flow of $CO_2$ through the endoscope 100 is similar to the flow of air. In the neutral state, $CO_2$ gas flows backward up the gas supply tubing 240*c* to the connector portion 265, up the gas feed line 240*b*, and is vented through the gas/water valve 140 to atmosphere. In the first position, the user closes off the vent hole in the gas/water valve 140, and the $CO_2$ gas is flowed through the gas/water valve to the gas supply line 240*a* in the endoscope shaft 100*a* and out the gas/lens wash nozzle 220 at the distal tip 100*c*. In the second position, the user depresses the valve 140 to the bottom of the valve well 135, keeping the vent hole in the gas/water valve closed off. The second position blocks the $CO_2$ gas supply to both atmosphere and the gas supply line 240*a* in the endoscope 100, and opens up the gas/water valve 140 to allow lens wash water to pass through to the lens wash supply line 245*a* in the endoscope shaft 100*a* and out the gas/lens wash nozzle 220 at the distal tip 100*c*. Gas (pressure) in the reservoir 405 is maintained by delivery gas through alternative gas (e.g., $CO_2$) supply tubing 415. The irrigation function may be accomplished in a similar manner as the operation described above with respect to FIG. 3D.

Figure 5A:
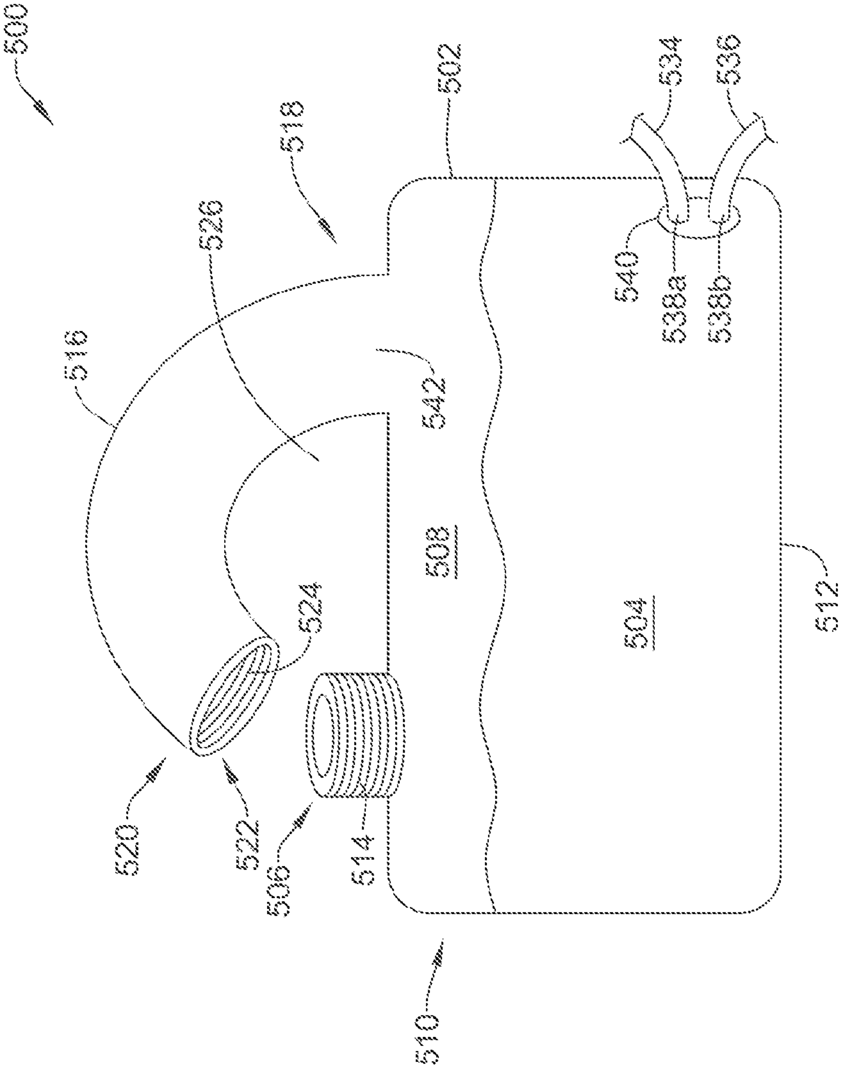
FIG. 5A depicts a side view of an illustrative refillable fluid reservoir.
Figure 5B:
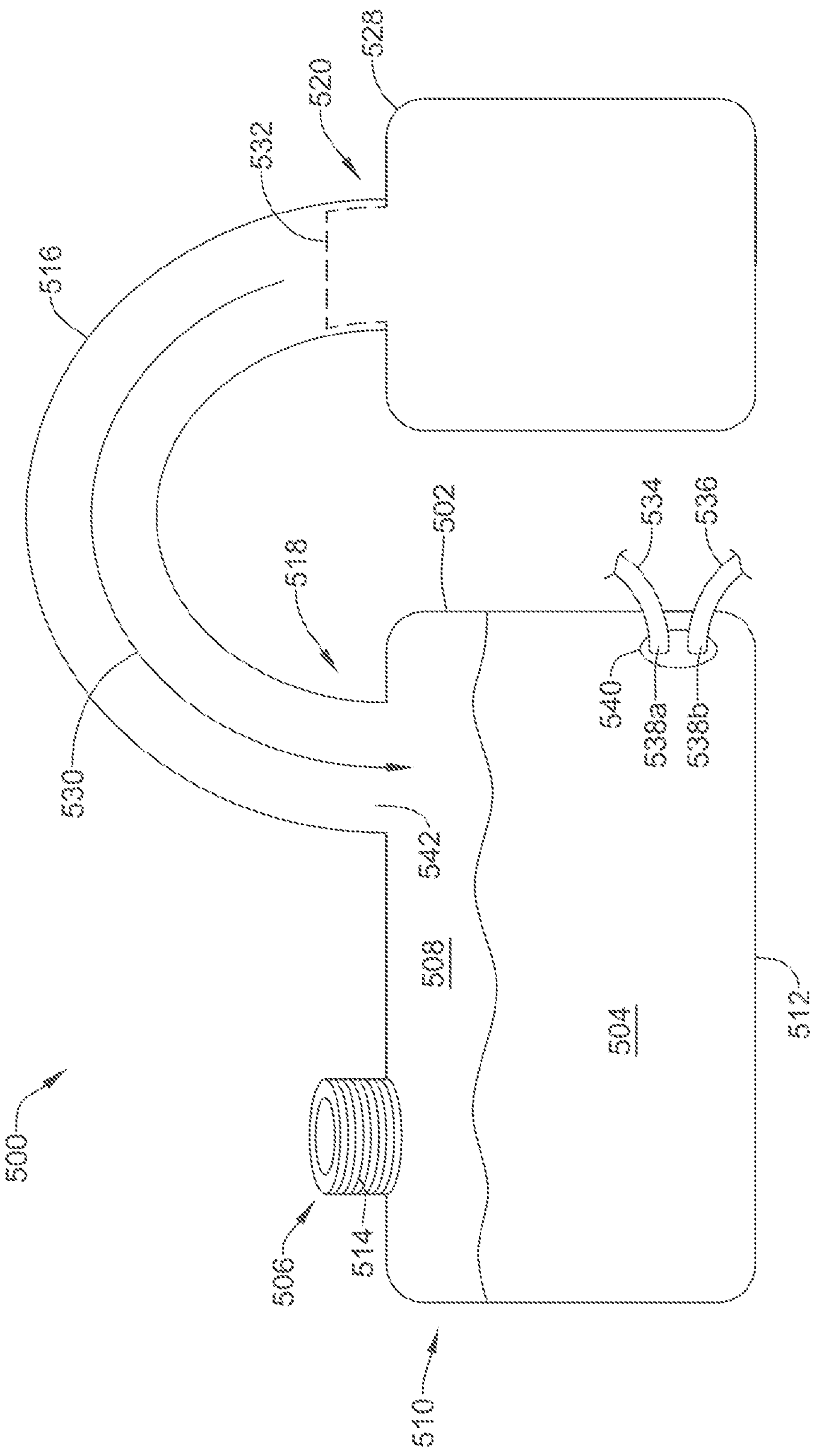
FIG. 5B depicts a side view of the illustrative reservoir of FIG. 5A coupled with a water bottle.

As described above, it may be desirable to reduce opportunities for contamination to the tube set 240*c*, 245*c*, 320, 410, 415 during replacement of the water reservoir by providing a refillable and/or larger volume water reservoir 270, 305, 405. FIG. 5A depicts a side view of an illustrative refillable fluid reservoir 500. FIG. 5B depicts a side view of the illustrative reservoir 500 coupled with a water bottle 528. The reservoir 500 may be configured to be used in an endoscopic system and includes components similar to the endoscope and endoscope systems described with regard to FIGS. 1-4; however, not all features may be described or shown here if not pertinent to the fluid circuit of the system. The reservoir 500 includes a container 502 configured to hold a fluid 504. The container 502 may be formed from a lightweight, flexible material, such as, but not limited to low density polyethylene (LDPE), thermoplastic polyurethane (TPU), silicone, polyethylene terephthalate (PET), aluminum, nylon, polyethylene (PE), or combinations thereof, etc. In other embodiments, the reservoir 500 may be formed from a rigid or semi-rigid material. In some embodiments, the container 502 may be entirely translucent, entirely opaque, or combinations thereof.

The reservoir 500 may further include a port 506. In some embodiments, the port 506 may be in fluid communication with an interior 508 of the container 502. However, this is not required. In some embodiments, the port 506 may not provide access to the interior 508 of the container. The port 506 may extend away from a top portion 510 of the container 502 in a direction opposite from a bottom portion 512 of the container 502. The port 506 may include a coupling mechanism 514, such as, but not limited to, a plurality of external threads. Other coupling mechanisms may be used as desired, such as, but not limited to, one or more grooves configured to receive one or more raised protrusions, one or more raised protrusions configured to be received in one or more mating grooves, friction fits, etc.

The reservoir 500 may further include a flexible tube 516. The flexible tube 516 may extend from a first end 518 coupled to the top portion 510 of the container 502 adjacent to an opening 542 in the container 502 to a second end 520 and defining a lumen 522 (FIG. 5A) therethrough. In some cases, the flexible tube 516 may be formed as single monolithic structure with the container 502. In other embodiments, the first end 518 of the flexible tube 516 may be coupled to the container 502. For example, the first end 518 of the flexible tube 516 may be rotatably coupled to the container 502. The lumen 522 may be configured to be in selective fluid communication with the interior 508 of the container 502. The second end 520 of the flexible tube 516 may include a coupling mechanism 524, such as, but not limited to, a plurality of internal threads. Other coupling mechanisms may be used as desired, such as, but not limited to, one or more grooves configured to receive one or more raised protrusions, one or more raised protrusions configured to be received in one or more mating grooves, friction fits, etc. The second end 520 of the flexible tube 516 may be configured to be selectively coupled to the port 506 or to a water bottle 528 (FIG. 5B). For example, when the reservoir 500 is in use, the second end 520 of the flexible tube 516 may be coupled to the port 506. This may seal the container 502 so that the interior 508 can be pressurized to provide lens wash fluid as well as maintain sterility of the lumen 522 of the flexible tube. It is further contemplated that when the second end 520 of the flexible tube 516 is coupled to the port 506, the flexible tube 516 may function as a handle. The flexible tube 516 may then receive a hand or a hook through an opening 526 defined by the space between the flexible tube 516 and the top portion 510 of the container 502. In some embodiments, when coupled to the port 506, the flexible tube 516 may be configured to couple to a hook or other mechanism on the endoscope tower. This may elevate the reservoir to reduce footprint on floor of the procedure room and improve ergonomics since the user may no longer need to bend down to the floor to interface with the reservoir.

When it is desired to fill or refill the reservoir 500, the second end 520 of the flexible tube 516 may be uncoupled from the port 506 such that the flexible tube 516 is free from the port 506 and coupled to a water bottle 528. The flexible tube 516 may be bent, rotated, or otherwise manipulated to bring the second end 520 to the mouth 532 of the water bottle 528. Alternatively, or additionally, in some cases, the mouth of the water bottle 528 may be brought towards the second end of the flexible tube 516. It is contemplated that the second end 520 of the flexible tube 516 may be coupled to the water bottle 528 while the water bottle 528 remains in an upright orientation. This may limit spills that may occur if the water bottle 528 is tipped for pouring and/or coupling. Once the second end of the flexible tube 516 is coupled to the water bottle 528, the water bottle 528 may be inverted to allow water to flow from an interior of the water bottle 528, through the lumen 522 of the flexible tube 516, and into the interior 508 of the container 502, as shown at flow path 530. In other examples, the water bottle 528 may be squeezed or compressed to move water from the interior thereof through the lumen 522 of the flexible tube 516, and into the interior 508 of the container 502, as shown at flow path 530. When the port 506 include a through hole to provide fluid communication with the interior 508 of the container 502, the port 506 may function as vent or pressure relief as water is flowing into the container 502. In other embodiments, the port 506 acts to secure the second end 520 of the flexible tube 516, thereby protecting the second end 520 from contaminants it may be exposed to in the room during a procedure and allowing for pressurization of the container 502, without providing fluid communication with the interior 508 of the container 502.

The reservoir 500 may be connected in fluid communication with a gas supply/alternate gas supply tubing (or gas supply tubing) 534 and a lens wash supply/irrigation supply tubing (or water supply tubing) 536. The gas supply tubing 534 extends from a second end external to the reservoir 500 through a reservoir opening **538*a* in the container 502. The gas supply tubing 534 may extend into the remaining fluid in the container 502. For example, the opening 538*a* may be at a bottom or side of the container 502 such that the gas supply tubing 534 terminates within the fluid with gas bubbling up through the fluid to pressurize the container. However, in some cases, the gas supply tubing 534 may be located adjacent the top portion 510 of the container 502 and may terminate within a reservoir gap, at or below the opening through which the gas supply tubing 534 extends, but not extending into the remaining fluid in the container 502. A lumen extends through the gas supply tubing 534 for receiving a flow of air and/or gas therethrough. The lumen of the gas supply tubing 534 is in operative fluid communication with the interior 508 of the reservoir 500. The water supply tubing 536 extends from a second end external to the reservoir 500 through a reservoir opening 538*b*, terminating in a first end within the remaining fluid at or substantially at a bottom portion 512 of the container 502. In some embodiments, the water supply tubing 536 may terminate at the opening 538*b*. For example, when the opening 538*b* is at or adjacent to the bottom portion 512 of the container 502 a dip tube may not be required. However, when the opening 538*b* is adjacent the top portion 510 of the container 502, a dip tube may be required. A lumen extends through the water supply tubing 536 for receiving a flow of fluid therethrough. The lumen of the water supply tubing 536 is in selective operative fluid communication with the bottom portion 512 of the container 502. In the illustrated embodiment, the gas supply tubing 534 and the water supply tubing 536 may extend in a side by side arrangement and enter the container 502 through separate openings 538*a*, 538*b*. However, this is not required. In some cases, the gas supply tubing 534 and the water supply tubing 536 may be enter the container through a single or common opening. For example, the gas supply tubing 534 and the water supply tubing 536 may be coaxially arranged. The openings 538*a*, 538*b* may include a grommet or heat seal 540 configured to seal the container 502 about the tubing 534, 536** in a fluid and pressure tight manner.

A portion of a gas supply tubing 534 and a portion of the water supply tubing 536 may extend from the reservoir 500, respectively, and may be connected in fluid communication with the endoscope at gas/lens wash connection on the connector portion 265 of the umbilical. The gas supply tubing 534 is connected in fluid communication with a gas pump (not explicitly shown) and gas feed line (not explicitly shown), and the water supply tubing 536 is connected in fluid communication with lens wash feed line (not explicitly shown), within connector portion 265. While not explicitly shown, irrigation supply tubing may be coupled to the water supply tubing 536 via a manifold to supply irrigation fluid from the reservoir 500 or a separate irrigation supply tubing may be provided that terminates at the container 502 and is in fluid communication with the interior 508 of the container 502.

The water bottle 528 and the flexible tube 516 may be held in place (if elevated) until all the water is transferred from the water bottle 528 to the container 502 through the flexible tube 516. Once complete, the water bottle 528 can be discarded and the second end 520 of the flexible tube 516 may be coupled with the port 506 to protect the second end 520 from contaminants it may be exposed to in the room during a procedure and to allow for pressurization of the container 502. The second end 520 of the flexible tube 516 may not be uncoupled from the port 506 until additional water transfer to the reservoir 500 is needed.

The refilling of the reservoir 500 may be performed during a procedure or between procedures, as necessary. The water may be sterile or non-sterile, as desired. For example, sterile water may be used for therapeutic procedures while non-sterile water may be used for diagnostic procedures. It is contemplated that refilling the reservoir 500 with sterile or non-sterile water may create more flexibility and reduce the need to have as much sterile water in storage. Further, refilling the reservoir 500 via the flexible tube 516 may also remove the need to disconnect the reservoir 500 from the tubing 534, 536 throughout the day eliminating or greatly reducing the possibility of cross contamination by removing the need to replace the water container.

Figure 6:
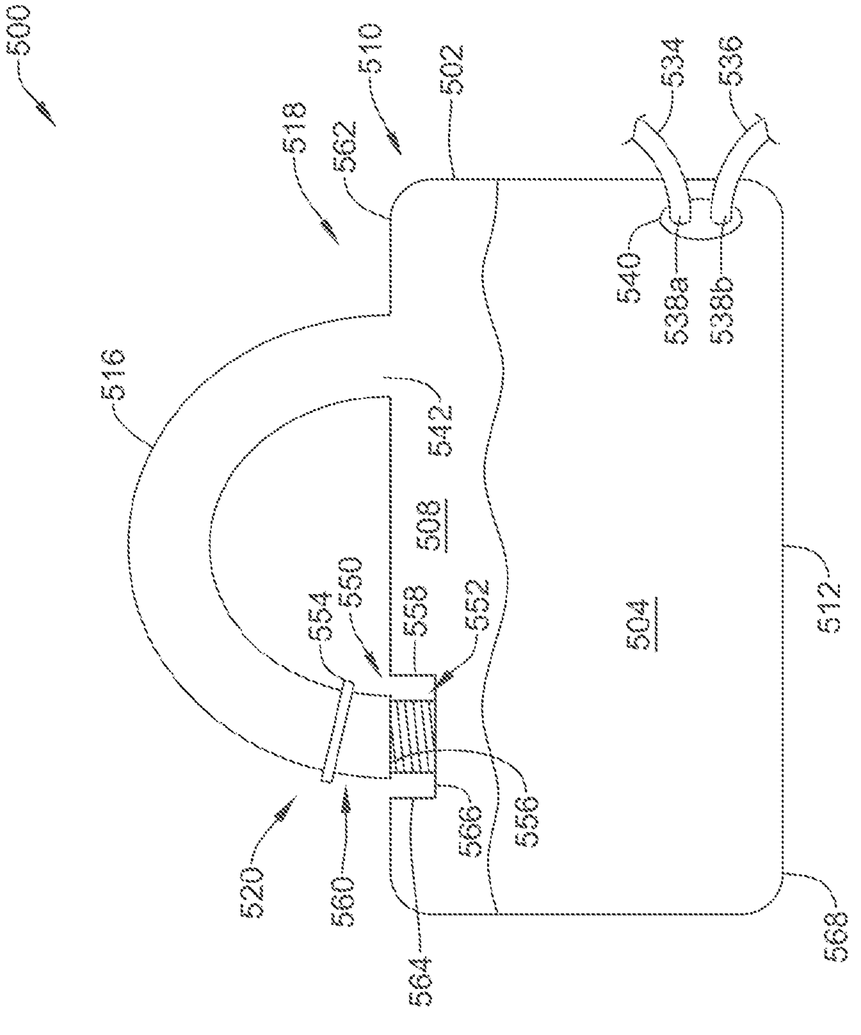
FIG. 6 is a side view of the illustrative reservoir of FIG. 5A having an alternative port and coupling mechanism for coupling the second end of the flexible tube to the port.

FIG. 6 is a side view of the illustrative reservoir 500 of FIG. 5A having an alternative port 550 and coupling mechanism 560 for coupling the second end 520 of the flexible tube 516 to the port 550. The port 550 may be disposed within a recess 558 formed in the top portion 510 of the container 502. The recess 558 may extend from an open first end 564 at the top 562 of the container 502 to a second end 566 offset from the top 562 of the container 502. The second end 566 of the recess 558 may be positioned between the top 562 and the bottom 568 of the container 502. The port 550 may further include a plurality of external threads 552.

The second end 520 of the flexible tube 516 may include a rotatable collar 554. The rotatable collar 554 may be configured to spin or rotate independently of a main body of the flexible tube 516. For example, the rotatable collar 554 may be an annular collar disposed at least partially about an outer surface of the flexible tube 516. The rotatable collar 554 may extend distally beyond the second end 520 of the flexible tube 516. The rotatable collar 554 may further include a plurality of internal threads 556. The plurality of internal threads 556 may be configured to threadably engage external threads 552 on the port 550. It is contemplated that the rotatable collar 554 may also be used with the port 506 of FIG. 5A.

Figure 7A:
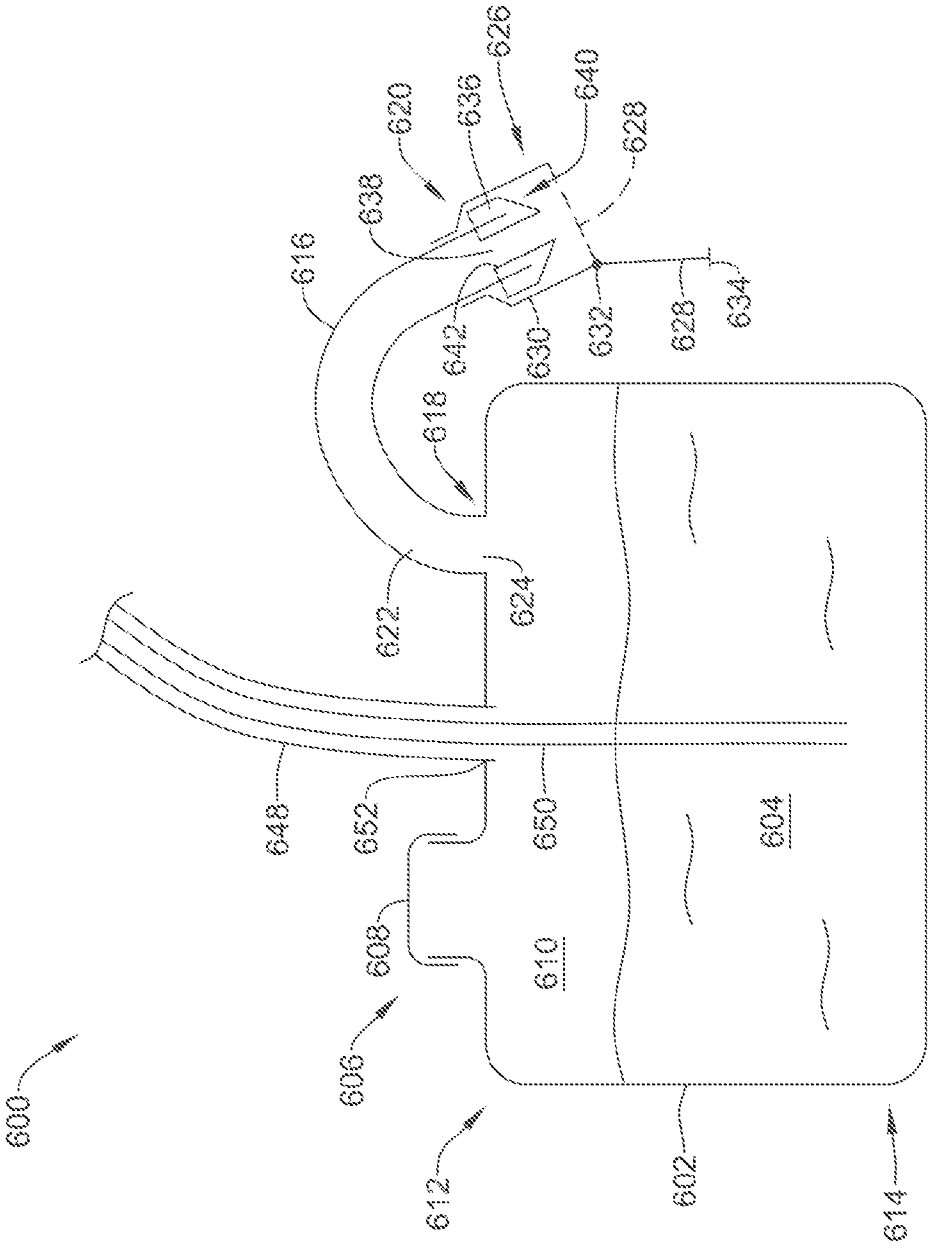
FIG. 7A depicts a side view of another illustrative refillable fluid reservoir.
Figure 7B:
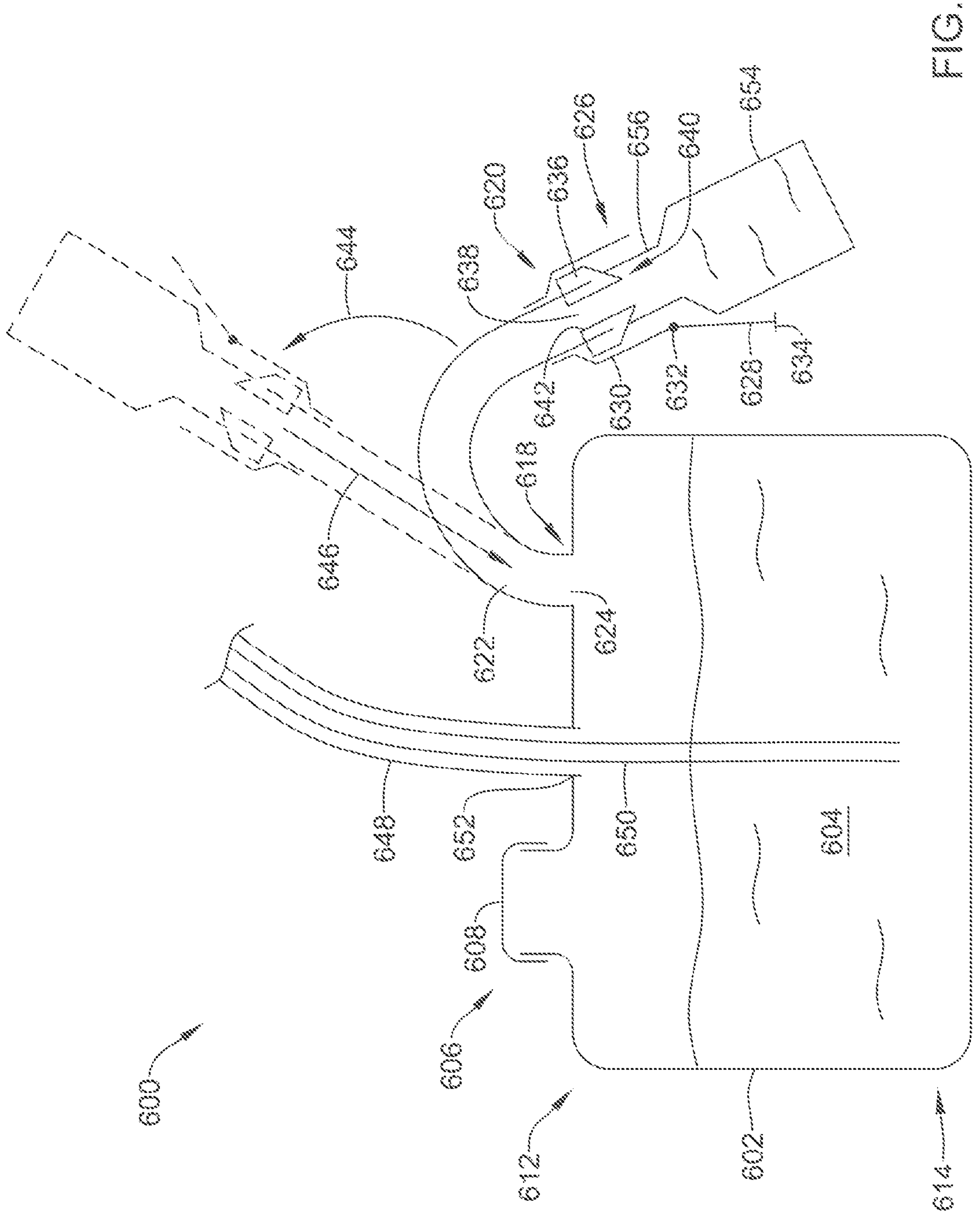
FIG. 7B depicts a side view of the illustrative reservoir of FIG. 7A coupled with a water bottle.

FIG. 7A depicts a side view of another illustrative refillable fluid reservoir 600. FIG. 7B depicts a side view of the illustrative reservoir 600 coupled with a water bottle 654. The reservoir 600 may be configured to be used in an endoscopic system and includes components similar to the endoscope and endoscope systems described with regard to FIGS. 1-4; however, not all features may be described or shown here if not pertinent to the fluid circuit of the system. The reservoir 600 includes a container 602 configured to hold a fluid 604. The container 602 may be formed from a lightweight, flexible material, such as, but not limited to low density polyethylene (LDPE), thermoplastic polyurethane (TPU), silicone, polyethylene terephthalate (PET), aluminum, nylon, polyethylene (PE), or combinations thereof, etc. In other embodiments, the reservoir 600 may be formed from a rigid or semi-rigid material. In some embodiments, the container 602 may be entirely translucent, entirely opaque, or combinations thereof.

The reservoir 600 may further include a port 606 having a removable cap 608. The cap 608 may be formed from a rigid material and may be configured to form a fluid tight seal with the port 606. The cap 608 may be configured to threadably engage the port 606, form a friction fit with the port 606, form a snap fit with the port 606, or otherwise releasably engage the port 606. In some embodiments, the cap 608 may be a self-sealing one-way valve. In other embodiments, the cap 608 may be formed from a self-healing material. For example, a needle may be used to puncture a self-healing material, providing access to an interior 610 of the container 602, and once the needle is removed, the hole formed by the needle is sealed without user intervention. In some examples, the port 606 and/or cap 608 may be formed from polyethylene terephthalate (PET), polypropylene (PP), etc. Portions of the port 606 may extend into the container 602. The removable cap 608 may be removed to place a fluid source in selective fluid communication with the container 602 and allow fluid to be poured through a lumen of the port 606 and into the container 602. In the case of a cap 608 formed from a self-healing material, a needle may be used to puncture the cap 608 and place a fluid source in selective fluid communication with the container 602 and allow fluid to be poured into the container 602.

The reservoir 600 may further include a flexible tube 616. The flexible tube 616 may extend from a first end 618 coupled to the top portion 612 of the container 602 adjacent to an opening 624 in the container 602 to a second end 620 and defining a lumen 622 therethrough. In some cases, the flexible tube 616 may be formed as single monolithic structure with the container 602. In other embodiments, the first end 618 of the flexible tube 616 may be coupled to the container 602. For example, the first end 618 of the flexible tube 616 may be rotatably coupled to the container 602. The lumen 622 may be configured to be in selective fluid communication with the interior 610 of the container 602.

The second end 620 of the flexible tube 616 may include an actuatable cap 626. The cap 626 may be disposed over the second end 620 of the flexible tube 616 and may be actuatable to selectively expose the second end of the flexible tube 616. For example, the cap 626 may include a cover 628 pivotably coupled to a body 630 of the cap 626. The cover 628 may be pivoted about a hinge 632 between a closed configuration (shown in dashed lines in FIG. 7A) and an open configuration. In the closed configuration, the cover 628 may form a fluid tight seal with the body 630 so that the interior 610 can be pressurized to provide lens wash fluid. The cover 628 may include a latch 634 to maintain the cover 628 in the closed configuration. In some embodiments, the cover 628 may further include a sealing member disposed on an inner surface thereof. While the cap 626 has been described as including a pivotable cover 628, it is contemplated that other actuation mechanisms may be used to move the cap 626 between the closed and open configurations. For example, in some embodiments, the cap 626 may threadably engage the second end 620 of the flexible tube 616. In other embodiments, the cap 626 may be slid along the flexible tube 616 to expose the second end 620 thereof.

The second end 620 of the flexible tube 616 may further include an annular sealing plug 636. The annular sealing plug 636 may be formed from a soft durometer material capable of deforming about or forming a fluid-tight seal with the mouth 656 of a water bottle 654 (FIG. 7B). The annular sealing plug 636 may define an aperture 638 extending through a thickness thereof. The aperture 638 is in fluid communication with the lumen 622 of the flexible tube. In some cases, the annular sealing plug 636 may include a tapered distal end region 640. For example, the external surface of the distal end region 640 may decrease in cross-sectional dimension in a distal direction (e.g., in a direction opposite the first end 618 of the flexible tube 616). In some embodiments, the distal end region 640 may be a conical taper or may generally resemble a truncated cone. The reverse configuration is also contemplated in which the cross-sectional dimension of the external surface of the distal end region 640 increases in a distal direction. In yet another example, the distal end region 640 may have a convex or a concave shape. Alternatively, or additionally, the internal surface of the distal end region 640 may decrease or increase in cross-sectional dimension in a distal direction. For instance, the interior surface 642 of the annular sealing plug 636 may be tapered. For example, the interior surface 642 may taper such that the cross-sectional dimension of the aperture 638 decreases in a distal direction (e.g., in a direction opposite the first end 618 of the flexible tube 616). The reverse configuration is also contemplated in which the cross-sectional dimension of the aperture 638 of the annular sealing plug 636 increases in a distal direction.

When it is desired to fill or refill the reservoir 600, the actuatable cap 626 may be moved to the open configuration by actuating the cap 626 (e.g., unlatching, sliding, unscrewing, etc.). Once the cap 626 is open, the second end 620 of the flexible tube 616 may be exposed. The annular sealing plug 636 may be inserted over the mouth 656 of the water bottle 654, for example, where the cross-sectional dimension of the aperture 638 of the annular sealing plug 636 increases in a distal direction (e.g., in a direction opposite the first end 618 of the flexible tube 616). Alternatively, the annular sealing plug 636 may be inserted within the mouth 656 of the water bottle 654 as shown in FIG. 7B, for example, where the external surface of the distal end region 640 decreases in cross-sectional dimension in a distal direction (e.g., in a direction opposite the first end 618 of the flexible tube 616). It is contemplated that the shape of the distal end region 640 and/or the shape of the mouth 656 may determine whether the annular sealing plug 636 is disposed over or within the mouth 656 of the water bottle 654. The coupling of the second end 620 of the flexible tube 616 and the water bottle 654 may be performed with the second end 620 of the flexible tube 616 pointed at a downward angle, as shown in FIG. 7A. The flexible tube 616 may be bent, rotated, or otherwise manipulated to bring the second end 620 to the mouth 656 of the water bottle 654. Alternatively, or additionally, in some cases, the mouth of the water bottle may be brought towards the second end of the flexible tube 616. It is contemplated that the second end 620 of the flexible tube 616 may be coupled to the water bottle 654 while the water bottle 654 remains in an upright orientation. This may limit spills that may occur if the water bottle is tipped for pouring and/or coupling. Once the second end of the flexible tube 616 is coupled to the water bottle 654, the water bottle 654 and the second end 620 of the flexible tube 616 may be inverted or rotated together, as shown at arrow 644, to maintain the seal between the annular sealing plug 636 and the mouth 656 of the water bottle 654 such that the flexible tube 616 is pointed in an upwards direction, as shown in dashed lines in FIG. 7B. This may allow water to flow from an interior of the water bottle 654, through the lumen 622 of the flexible tube 616, and into the interior 610 of the container 602, as shown at flow path 646. This may allow for the transfer of water to be initiated via gravity. It is contemplated that the diameter of the flexible tube 616 may be large enough to allow high volumetric flow rates with nothing other than gravity aiding in the transfer. However, this is not required. In other examples, the water bottle 654 may be squeezed or compressed to move water from the interior thereof through the lumen 622 of the flexible tube 616, and into the interior 610 of the container 602, as shown at flow path 646. It is contemplated that during filling or refilling of the reservoir 600, the cap 608 may be removed from the port 606 to provide a vent.

The water bottle 654 and the flexible tube 616 may be held in place until all the water is transferred from the water bottle 654 to the container through the flexible tube 616. Once complete, the water bottle 654 can be discarded and the actuatable cap 626 may be moved to the closed configuration to protect the annular sealing plug 636 from contaminants it may be exposed to in the room during a procedure and to allow pressurization of the container 602, and the actuatable cap 626 may not be opened again until additional water transfer to the reservoir 600 is needed.

The reservoir 600 may be connected in fluid communication with a gas supply/alternate gas supply tubing (or gas supply tubing) 648 and a lens wash supply/irrigation supply tubing (or water supply tubing) 650. The gas supply tubing 648 extends from a second end external to the reservoir 600 through a reservoir opening 652 in the container 602. The shared gas supply tubing 648 may be located adjacent the top portion 612 of the container 602 and may terminate within a reservoir gap, at or below the opening 652, but not extending into the remaining fluid in the container 602. However, in some cases, the shared gas supply tubing 648 may extend into the remaining fluid in the container 602. For example, the opening 652 may be at a bottom portion 614 or side of the container 602 such that the shared gas supply tubing 648 terminates within the fluid with gas bubbling up through the fluid to pressurize the container. A lumen extends through the gas supply tubing 648 for receiving a flow of air and/or gas therethrough. The lumen of the gas supply tubing 648 is in operative fluid communication with the interior 610 of the reservoir 600. The water supply tubing 650 extends from a second end external to the reservoir 600 through the reservoir opening 652, terminating in a first end within the remaining fluid at or substantially at a bottom portion 614 of the container 602. In some embodiments, the water supply tubing 650 may terminate at the opening 652. For example, when the opening 652 is at or adjacent to the bottom portion 614 of the container 602 a dip tube may not be required. A lumen extends through the water supply tubing 650 for receiving a flow of fluid therethrough. The lumen of the water supply tubing 650 is in selective operative fluid communication with the bottom portion 614 of the container 602. In the illustrated embodiment, the gas supply tubing 648 and the water supply tubing 650 may be enter the container through a single or common opening 652. However, this is not required. For example, the gas supply tubing 648 and the water supply tubing 650 may be coaxially arranged. In some cases, the gas supply tubing 648 and the water supply tubing 650 may extend in a side by side arrangement and enter the container 602 through separate openings. The opening 652 may include a grommet or heat seal (not explicitly shown) configured to seal the container 602 about the tubing 648, 650 in a fluid and pressure tight manner.

A portion of a gas supply tubing 648 and a portion of the water supply tubing 650 may extend from the reservoir 600, respectively, and may be connected in fluid communication with the endoscope at gas/lens wash connection on the connector portion 265 of the umbilical. The gas supply tubing 648 is connected in fluid communication with a gas pump (not explicitly shown) and gas feed line (not explicitly shown), and the water supply tubing 650 is connected in fluid communication with lens wash feed line (not explicitly shown), within connector portion 265. While not explicitly shown, irrigation supply tubing may be coupled to the water supply tubing 650 via a manifold to supply irrigation fluid from the reservoir 600 or a separate irrigation supply tubing may be provided that terminates at the container 602 and is in fluid communication with the interior 610 of the container 602.

The refilling of the reservoir 600 may be performed during a procedure or between procedures, as necessary. The water may be sterile or non-sterile, as desired. For example, sterile water may be used for therapeutic procedures while non-sterile water may be used for diagnostic procedures. It is contemplated that refilling the reservoir 600 with sterile or non-sterile water may create more flexibility and reduce the need to have as much sterile water in storage. Further, refilling the reservoir 600 via the flexible tube 616 may also remove the need to disconnect the reservoir 600 from the tubing 648, 650 throughout the day eliminating or greatly reducing the possibility of cross contamination by removing the need to replace the water container.

As will be appreciated, the lengths of irrigation, lens wash, gas supply, alternate gas supply tubing may have any suitable size (e.g., diameter). In addition, the sizing (e.g., diameters) of the tubing may vary depending on the application. In one non-limiting embodiment, the irrigation supply tubing may have an inner diameter of approximately 6.5 mm and an outer diameter of 9.7 mm. The lens wash supply tubing may have an inner diameter of approximately 5 mm and an outer diameter of 8 mm. The gas supply tubing may have an inner diameter of approximately 2 mm and an outer diameter of 3.5 mm. The alternative gas supply tubing may have an inner diameter of approximately 5 mm and an outer diameter of 8 mm.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

In the foregoing description and the following claims, the following will be appreciated. The phrases "at least one", "one or more", and "and/or", as used herein, are open-ended expressions that are both conjunctive and disjunctive in operation. The term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The foregoing discussion has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. One skilled in the art will appreciate that the disclosure may be used with many modifications of structure, arrangement, proportions, materials, components, and otherwise, used in the practice of the disclosure, which are particularly adapted to specific environments and operative requirements without departing from the principles of the present disclosure. For example, elements shown as integrally formed may be constructed of multiple parts or elements shown as multiple parts may be integrally formed, the operation of elements may be reversed or otherwise varied, the size or dimensions of the elements may be varied, and features and components of various embodiments may be selectively combined. The presently disclosed embodiments are therefore to be considered in all respects as illustrative and not restrictive, the scope of the claimed invention being indicated by the appended claims, and not limited to the foregoing description.

The following claims are hereby incorporated into this Detailed Description by this reference, with each claim standing on its own as a separate embodiment of the present disclosure. In the claims, the term "comprises/comprising" does not exclude the presence of other elements or steps. Furthermore, although individually listed, a plurality of means, elements or method steps may be implemented by, e.g., a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

What is claimed is:

1. A fluid reservoir arranged and configured to couple to an endoscope for use in an endoscopic procedure, the fluid reservoir comprising:

a container configured to contain a fluid and having a bottom portion and a top portion;

a lens water supply tube including a first end, a second end, and a first lumen extending therethrough, wherein the first lumen is in fluid communication with the bottom portion of the container and the second end of the lens water supply tube is positioned external to the container;

a gas supply tube including a first end, a second end, and a second lumen extending therethrough, wherein the second lumen is in operative fluid communication with an interior of the container and the second end of the gas supply tube is positioned external to the container;

a port positioned adjacent to the top portion of the container; and a flexible tube including a first end coupled to the top portion of the container, a second end, and a third lumen extending therethrough, wherein the third lumen of the flexible tube is configured to be in selective fluid communication with the interior of the container.

2. The fluid reservoir of claim 1, wherein the second end of the flexible tube is configured to be coupled to the port and configured to be uncoupled from the port.

3. The fluid reservoir of claim 2, wherein the second end of the flexible tube is configured to threadably engage the port.

4. The fluid reservoir of claim 1, wherein the second end of the flexible tube includes a rotatable collar.

5. The fluid reservoir of claim 1, wherein the second end of the flexible tube comprises an annular sealing plug in fluid communication with the third lumen of the flexible tube.

6. The fluid reservoir of claim 5, wherein the annular sealing plug is configured to form a seal with a water bottle.

7. The fluid reservoir of claim 5, further comprising an actuatable cap disposed over the annular sealing plug.

8. The fluid reservoir of claim 7, wherein the actuatable cap is configured to be opened to transfer water from a water bottle to the container and closed during use of the container.

9. A fluid reservoir arranged and configured to couple to an endoscope for use in an endoscopic procedure, the fluid reservoir comprising:

a container configured to contain a fluid and having a bottom portion and a top portion;

a lens water supply tube including a first end, a second end, and a first lumen extending therethrough, wherein the first lumen is in fluid communication with the bottom portion of the container and the second end of the lens water supply tube is positioned external to the container;

a gas supply tube including a first end, a second end, and a second lumen extending therethrough, wherein the second lumen is in operative fluid communication with an interior of the container and the second end of the gas supply tube is positioned external to the container;

a port positioned adjacent to the top portion of the container; and a flexible tube including a first end coupled to the top portion of the container, a second end, and a third lumen extending therethrough, wherein the third lumen of the flexible tube is configured to be in selective fluid communication with the interior of the container;

wherein the second end of the flexible tube is configured to be coupled to the port and configured to coupled with a secondary container, and when the second end of the flexible tube is coupled to the port, the flexible tube forms a handle for the container.

10. The fluid reservoir of claim 9, wherein the second end of the flexible tube is configured to threadably engage the port.

11. The fluid reservoir of claim 9, wherein the second end of the flexible tube includes a rotatable collar.

12. The fluid reservoir of claim 9, wherein the port includes a plurality of external threads.

13. The fluid reservoir of claim 9, wherein the first end of the flexible tube is rotatably coupled to the container.

14. The fluid reservoir of claim 9, wherein when the second end of the flexible tube is free from the port, the second end of the flexible tube is configured to be coupled to a water bottle.

* * * * *